United States Patent
Zuk et al.

(10) Patent No.: US 12,180,466 B2
(45) Date of Patent: *Dec. 31, 2024

(54) PLANT TISSUE COLLECTION, RNA EXTRACTION AND GENETIC ANALYSIS

(71) Applicant: WINFIELD SOLUTIONS, LLC, Shoreview, MN (US)

(72) Inventors: Jonathan Zuk, Hayfield, MN (US); Stephanie Wedryk, Shoreview, MN (US)

(73) Assignee: WinField Solutions, LLC, Arden Hills, MN (US)

( * ) Notice: Subject to any disclaimer, the term of this patent is extended or adjusted under 35 U.S.C. 154(b) by 350 days.

This patent is subject to a terminal disclaimer.

(21) Appl. No.: 17/556,710

(22) Filed: Dec. 20, 2021

(65) Prior Publication Data

US 2022/0112482 A1   Apr. 14, 2022

Related U.S. Application Data

(63) Continuation of application No. 15/906,777, filed on Feb. 27, 2018, now Pat. No. 11,242,517.

(51) Int. Cl.
  *C12N 15/10* (2006.01)
  *C12Q 1/6874* (2018.01)
  *C12Q 1/6895* (2018.01)

(52) U.S. Cl.
  CPC ....... *C12N 15/1003* (2013.01); *C12Q 1/6874* (2013.01); *C12Q 1/6895* (2013.01); *C12Q 2600/158* (2013.01)

(58) Field of Classification Search
  None
  See application file for complete search history.

(56) References Cited

U.S. PATENT DOCUMENTS

2019/0264192 A1   8/2019   Zuk et al.

OTHER PUBLICATIONS

Bogamuwa, et al. (Plant, cell & environment 36.8 (2013): 1507-1519). (Year: 2013).*

Ashraf, et al., "Pre-Sowing Seed Treatment—A Shotgun Approach to Improve Germination, Plant Growth, and Crop Yield Under Saline and Non-Saline Conditions", Advances in Agronomy, vol. 88, pp. 223-271, 2005, Elsevier Inc.

Basra, et al., "INfluence of Seed Pre-treatments with Plant Growth Regulators on Metabolic Alterations of Germinating Maize Embryos Under Stressing Temperature Regimes", Annals of botany 64.1, 1989, pp. 37-41.

Bogamuwa, et al., "The Arabidopsis tandem CCCH zinc finger proteins AtTZF4, 5 and 6 are involved in light-, abscisic acid- and gibberellic acid-mediated regulation of seed germination", Plant, cell & environment 36.8, 2013, pp. 1507-1519.

Dragićević, et al., "Differential Regulations of GS-GOGAT Gene Expression by Plant Growth Regulators in Arabidopsis Seedlings", Arch Biol Sci, vol. 68 No. 2, pp. 399-404, 2016.

Meng, et al., "A rapid TRIzol-based two-step method for DNA-free RNA extraction from Arabidopsis siliques and dry seeds", Biotechnology Journal 5.2, 2010, pp. 183-186.

Ogawa, Mikihiro et al., "Gibberellin Biosyntheses and Response during Arabidopsis Seed Germination", The Plant Cell 15. 7, 2003, pp. 1591-1604.

Suo, et al., "Plant Growth Regulators in Seed Coating Agent Affect Seed Germination and Seedling Growth of Sweet Corn", Applied ecology and environmental research 15.4, 2017, pp. 829-839.

Tian, et al., "Responses of Seed Germination, Seedling Growth, and Seed Yield Traits to Seed Pretreatment in Maize (*Zea mays L.*)", The Scientific World Journal vol. 2014, 2014, 9 pages.

Wang, et al., "Phytohormone-regulated B-amylase gene expression in rice", Plant molecular biology 31.5, 1996, pp. 975-982.

Wu et al. "Transcriptome analysis of hexaploid hulless oat in response to salinity stress." PLos ONE 12(2) Feb. 13, 2017, pp. 1-16.

* cited by examiner

*Primary Examiner* — Charles Logsdon
(74) *Attorney, Agent, or Firm* — Dorsey & Whitney LLP

(57) ABSTRACT

Methods of extracting ribonucleic acid from plant tissue involve treating multiple groups of plant seeds with different plant growth regulators. Each group of plant seeds can be treated with a different plant growth regulator. Methods further involve germinating the plant seeds to form seedlings, harvesting tissue samples from subgroups within each group of plant seeds and seedlings at different timepoints, and extracting total RNA from each harvested tissue sample. Methods can also involve sequencing the extracted RNA, determining an expression level of a plurality of genes relative to a negative control, and identifying a subset of differentially expressed genes at each distinct timepoint.

20 Claims, 4 Drawing Sheets

PLANT TISSUE COLLECTION, RNA EXTRACTION AND GENETIC ANALYSIS

CROSS-REFERENCE TO RELATED APPLICATIONS

This application is a continuation of U.S. application Ser. No. 15/906,777 filed on Feb. 27, 2018, issued as U.S. Pat. No. 11,242,517 on Feb. 8, 2022, entitled "PLANT TISSUE COLLECTION, RNA EXTRACTION AND GENETIC ANALYSIS" which is incorporated by reference herein, in its entirety and for all purposes.

TECHNICAL FIELD

Implementations relate to methods of collecting tissue samples and extracting RNA from plant seeds and seedlings exposed to various plant growth regulators. Particular implementations involve collecting tissue from specific portions of seeds and seedlings at defined timepoints during germination, extracting RNA from the tissue samples, and acquiring gene expression data from the extracted RNA.

BACKGROUND

Improving plant growth and development is a major focus of the agricultural industry. One approach to achieving robust growth involves applying growth stimulants to seeds and young plants. These substances may include plant growth regulators (PGRs), which typically comprise combinations of plant hormones that promote cellular growth processes like mitosis, and other substances including, for example, biostimulants, biologicals, and plant extracts. Optimization of the composition and application of PGRs is impeded, however, because the impact of PGRs on plant development at specific developmental stages is difficult to ascertain. As a result, suboptimal stimulant formulations are often applied at inopportune times during plant development, resulting in wasted product, possibly undesired results, and untapped growth potential.

SUMMARY

Figure 1:
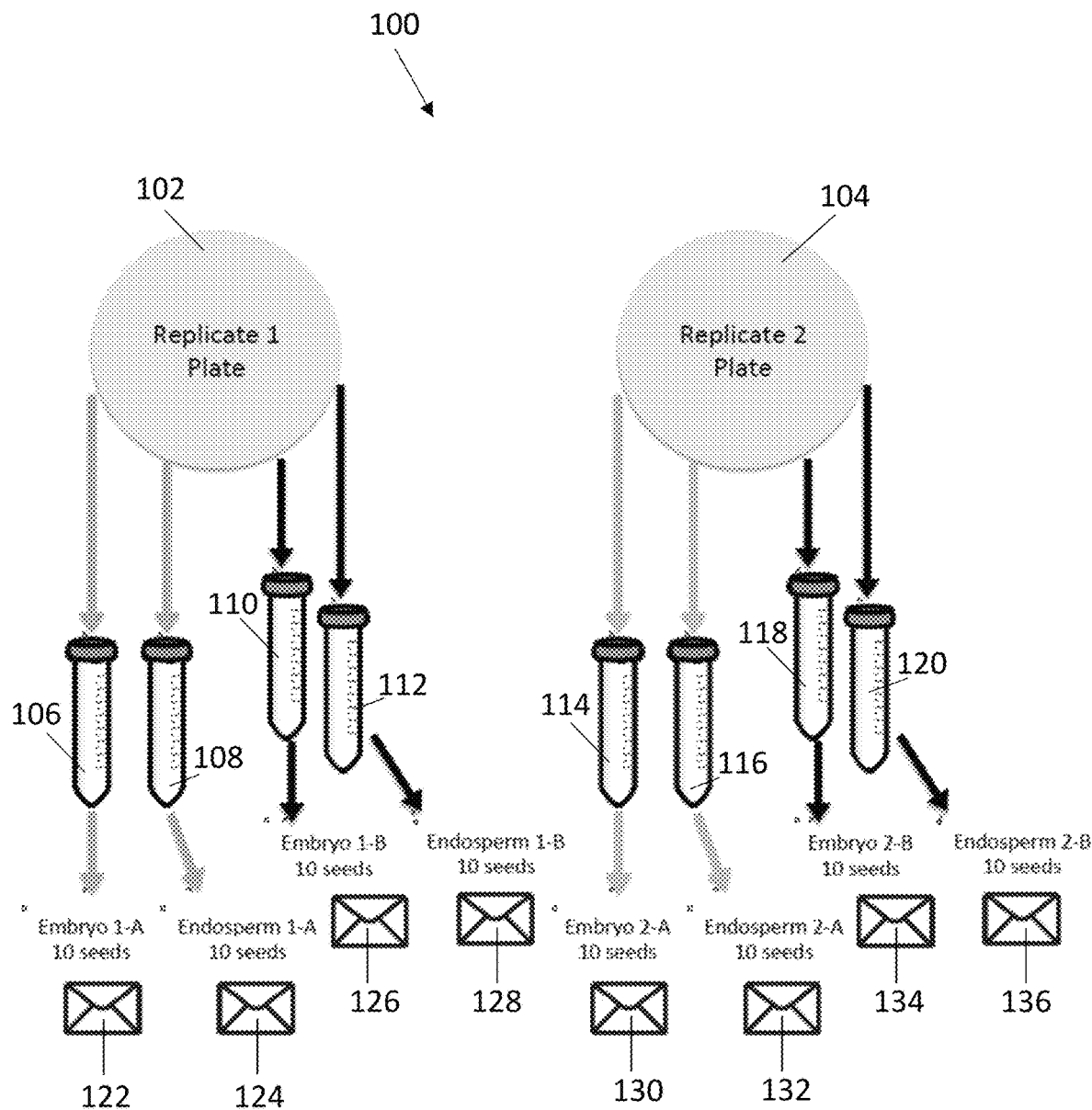
FIG. 1 is a diagram of a tissue harvesting scheme implemented in accordance with an example embodiment of the present invention.

Implementations provide approaches to harvesting tissue from germinating seeds and seedlings at distinct time points. Groups of seeds can be treated with different substances, such as plant growth regulators or components thereof, and subgroups within each group harvested at specific timepoints. Total RNA can be extracted from the harvested tissue for further analysis.

In accordance with some examples of the present disclosure, a method of extracting ribonucleic acid from plant tissue may involve treating multiple groups of plant seeds with different plant growth regulators. Each group of plant seeds can be treated with a different plant growth regulator. The method may further involve germinating the plant seeds to form seedlings and harvesting tissue samples from subgroups within each group of plant seeds and seedlings at different timepoints. Each subgroup can be harvested at a distinct timepoint. The method may additionally involve extracting total RNA from each harvested tissue sample.

In some examples, germinating the plant seeds may involve incubating the plant seeds between two layers of filter paper. In some embodiments, incubating the plant seeds may involve keeping the plant seeds in an incubator with no light for at least about 12 hours after an incubating period is initiated at a constant temperature of about 15.5° C. In some examples, incubating the plant seeds may involve keeping the plant seeds in an incubator programmed to apply alternating 12-hour cycles of light and dark at a constant temperature of about 15.5° C. beginning at about 72 hours after an incubating period is initiated. In some embodiments, harvesting tissue from subgroups within each group of plant seeds and seedlings at different timepoints may involve harvesting a first subgroup of plant seeds at a first timepoint, harvesting a second subgroup of plant seeds at a second timepoint, harvesting a third subgroup of plant seedlings at a third timepoint, harvesting a fourth subgroup of plant seedlings at a fourth timepoint, and harvesting a fifth subgroup of plant seedlings at a fifth timepoint. In some examples, at least a portion of an embryo and an endosperm can be harvested from each plant seed in the first subgroup. In some embodiments, at least a portion of an embryo and an endosperm can be harvested from each plant seed in the second subgroup. In some examples, at least a portion of a radicle can be harvested from each seedling in the third subgroup. In some embodiments, at least a portion of a radicle and coleoptile can be harvested from each seedling in the fourth subgroup. In some examples, at least a portion of a radical and a coleoptile can be harvested from each seedling in the fifth subgroup. In some embodiments, the first timepoint is about 12 hours after an incubating period is initiated, the second timepoint is about 24 hours after an incubating period is initiated, the third timepoint is about 96 hours after an incubating period is initiated, the fourth timepoint is about 120 hours after an incubating period is initiated, and the fifth timepoint is about 144 hours after an incubating period is initiated.

In some embodiments, at least one of the plant growth regulators can be a component of another one of the plant growth regulators. In some examples, at least one of the plant growth regulators can include kinetin, gibberellic acid, indole-3-butyric acid, or a combination thereof. In some embodiments, methods may further involve freezing the tissue in liquid nitrogen after harvesting. In some embodiments, extracting total RNA from each harvested tissue sample can involve treating each harvested tissue sample with TRIzol and chloroform.

In accordance with some examples of the present disclosure, a method of determining an impact of a plant growth regulator on germination can involve treating multiple groups of plant seeds with different plant growth regulators. Each group of plant seeds can be treated with a different plant growth regulator. The method can further involve germinating the plant seeds to form seedlings, and harvesting tissue samples from subgroups within each group of plant seeds and seedlings at different timepoints. Each subgroup can be harvested at a distinct timepoint. The method can also involve extracting total RNA from each harvested tissue sample, sequencing the extracted RNA, determining an expression level of a plurality of genes relative to a negative control, and identifying a subset of differentially expressed genes at each distinct timepoint.

In some examples, harvesting tissue from subgroups within each group of plant seeds and seedlings at different timepoints can involve harvesting a first subgroup of plant seeds at a first timepoint, harvesting a second subgroup of plant seeds at a second timepoint, harvesting a third subgroup of plant seedlings at a third timepoint, harvesting a fourth subgroup of plant seedlings at a fourth timepoint, and harvesting a fifth subgroup of plant seedlings at a fifth timepoint. In some embodiments, at least a portion of an embryo and an endosperm is harvested from each plant seed in the first subgroup, at least a portion of an embryo and an endosperm is harvested from each plant seed in the second subgroup, at least a portion of a radicle is harvested from each seedling in the third subgroup, at least a portion of a radicle and coleoptile is harvested from each seedling in the fourth subgroup, and at least a portion of a radical and a coleoptile is harvested from each seedling in the fifth subgroup. In some embodiments, the first timepoint is about 12 hours after an incubating period is initiated, the second timepoint is about 24 hours after an incubating period is initiated, the third timepoint is about 96 hours after an incubating period is initiated, the fourth timepoint is about 120 hours after an incubating period is initiated, and the fifth timepoint is about 144 hours after an incubating period is initiated. In some examples, at least one of the plant growth regulators can include about 0.09 wt % cytokinin, about 0.03 wt % gibberellic acid, and about 0.045 wt % indole-3-butyric acid.

DETAILED DESCRIPTION

The techniques implemented according to the present disclosure involve harvesting tissue from germinating seeds and nascent seedlings and extracting RNA therefrom. Prior to harvest, the seeds can be divided into different treatment groups, each treatment group exposed to a different PGR or component thereof. Each treatment group can be divided into subgroups defined by the distinct timepoint at which tissue from each subgroup is harvested. The timepoints defining each subgroup are the same across all treatment groups. By extracting RNA at specific timepoints from germinating plants treated with different PGRs, changes in gene expression can be monitored over time and the chronological effects of applying different PGRs elucidated.

The methods described herein extract RNA from plants separately exposed to different PGRs, but the protocols are not strictly limited to PGRs. For example, the effects of various plant treatment substances, including but not limited to hormones, pesticides, insecticides, fungicides, herbicides, chemicals, biostimulants, biologicals, and plant extracts, etc., can be elucidated by adhering to the methods described herein. The extraction protocols disclosed herein are also not strictly limited to one particular plant type, and can be applied to various plant species, including but not limited to corn (maize), beans, wheat, barley, alfalfa, and other crop species.

Separate treatment groups of seeds can be defined by the particular PGR(s) applied to the seeds. Before germinating the seeds, stock solutions for each treatment can be prepared. The solutions can comprise PGRs or PGR components, and the concentration of each solution can be the same or different. In some examples, the solutions can include gibberellic acid (GA), indole-3-butyric acid (IBA), one or more types of cytokinin, e.g., kinetin, and/or combinations thereof, each of which may be considered a PGR component. GA stimulates cell division and elongation in leaves and stems, IBA stimulates root formation and increases cell elongation, and cytokinin promotes cell division and leaf expansion. Separate treatment solutions can also comprise identical components, but mixed in different ratios. A negative control solution containing no PGRs is also prepared for comparative purposes. Various liquids can be used to prepare the treatment and control solutions, e.g., water (MilliQ), propylene glycol, various buffers, and/or combinations thereof. Proprietary PGRs may be used and in some embodiments may not require dilution prior to application. Various PGR and non-PGR products are within the scope of this disclosure. Active ingredients in one or more PGR products can include complex polymeric polyhydroxy acids (CPPA) and cytokinin, for example. The amount of each active ingredient may vary. For instance, CPPA can be included at about 0.05 wt % to about 0.2 wt %, about 0.08 wt % to about 0.15 wt %, or about 0.11 wt %, and cytokinin can be included at about 0.005 wt % to about 0.05 wt %, about 0.008 wt % to about 0.02 wt %, or about 0.01 wt %. In additional proprietary mixes, active ingredients may include cytokinin, GA, and/or IBA. The amount of cytokinin may range from about 0.03 wt % to about 0.2 wt %, about 0.06 wt % to about 0.12 wt %, or about 0.09 wt %. The amount of GA may range from about 0.005 wt % to about 0.15 wt %, about 0.01 wt % to about 0.06 wt %, or about 0.03 wt %. The amount of IBA may range from about 0.008 wt % to about 0.17 wt %, about 0.01 wt % to about 0.07 wt %, or about 0.045 wt %. Other treatment substances comprising PGR components, e.g., a cytokinin, GA, and/or IBA, may be mixed with at least one or more additional liquids and shaken and/or incubated to fully solubilize the PGRs. The stock solutions can be shaken and/or incubated for various periods of time until homogenous. In one example, the solutions are shaken at about 150 rpm at 32° C. for about 8 to about 14 hours.

Aliquots of the treatment and control solutions can be added to separate plates, e.g., petri dishes, used to contain the seeds for the duration of the incubation period. The number of plates prepared for each treatment depends on the desired sample size and the number of replicates desired. For example, 2 replicates may be prepared for each treatment subgroup. In some examples, 10 plates can be prepared for each treatment type. To ensure that excess solution is available, a volume of solution sufficient to fill about 14 plates can be prepared. According to such examples, about 196 mL of each solution can be prepared.

A single treatment solution or control solution is added to each plate. The amount of solution added to each plate can vary depending on, for example, the number of seeds added to each plate. In specific embodiments, 30 seeds and about 14 mL of solution can be added to each plate. Each plate can be lined with two sheets of filter paper, one placed below the seeds and one above. About 7 mL of solution can be added to the first, bottom sheet of filter paper and about 7 mL can be added to the second, top sheet of filter paper. Various types of filter paper can be used, including for example Whatman Filter Paper, Grade 113, provided the filter paper retains moisture throughout the incubation period. Seeds are placed between the two filter paper layers lining each plate, with the embryo of each seed facing upward. The arrangement of seeds may vary, but generally the seeds may be placed on the bottom layer of filter paper such that the space between each seed is maximized. In some embodiments, seeds may be arranged in rows across each plate. The number of seeds included in each row may depend on the width of the plate across a particular row. For instance, row 1 may include 4 seeds, row 2 may include 5 seeds, rows 3 and 4 may include 6 seeds, row five may include 5 seeds, and row 6 may include 4 seeds. Each plate may be covered with a plate cover and/or parafilm.

The concentration of each treatment solution can be formulated such that a specific amount of each treatment substance is applied to each seed. In one example, about 0.35 to about 1.8 µL or µg of a given treatment substance may be applied to each seed. The per-seed amount of each treatment substance is consistent for all subgroups within a given treatment group.

After adding the seeds and treatment solutions to each plate, the plates are placed in an incubator. The incubator conditions may vary, and can be changed one or more times throughout the incubation period. For at least an initial portion of the incubation period, e.g., the first 12, 24, 48, or 96 hours of incubation, the seeds can be incubated in the dark at about 15.5° C. In additional examples, the seeds may be incubated at temperatures ranging from about 10° C. to about 22° C. The incubator settings may be modified as necessary to evaluate the responsiveness of the seeds to particular environmental conditions of interest when subjected to specific treatment solutions. For instance, the incubator may not be dark for an initial period, and in some examples, may be light for an initial period and dark for a later period. In some embodiments, the incubator may be programmed to alternate between light and dark periods. In some embodiments, the seeds may be subjected to periods of moisture and dryness, or specific periods of hot, dry conditions and/or cool, wet conditions, for example.

Each treatment subgroup is incubated for a specific period of time, which was optimized to enable the controlled collection of gene expression data embodying specific aspects of a plant growth on a consistent basis. The number of timepoints, and thus distinct subgroups, may vary. In at least one example, 5 subgroups are harvested at timepoints of about 12, 24, 96, 120 and 144 hours, respectively, after initiation of the incubation period. The timepoints defining each subgroup are the same across each treatment group so that tissue is harvested at the same timepoints in all treatment groups, thus providing a controlled means of collecting gene expression data. The timepoints selected for tissue harvesting are critical for extracting RNA samples that capture changes in gene expression that are at least partially responsible for driving the phenotypic changes typically used to define discrete stages of healthy plant development. For example, by harvesting tissue after 96 hours of incubation, changes in gene expression may be linked with development of a seedling's coleoptile and the impact of a particular PGR composition on such development. In some examples, even small deviations from the predefined timepoints may yield significantly different results. Prior techniques for evaluating PGR effectiveness have relied primarily on visual monitoring of the final traits of fully developed plants exposed to PGRs, thus failing to elucidate the molecular impact of various PGRs at specific stages of growth. In additional examples, the timepoints can be varied to evaluate different stages of plant growth responsive to various treatment substances and/or environmental conditions.

After about 12 hours of incubation, tissue may be harvested from the embryo and/or endosperm of the seeds assigned to the 12-hour subgroup within each treatment and control group. Aliquots of liquid nitrogen can be prepared, which will be used to freeze the tissue samples immediately after harvesting. Seeds are removed individually from the plates, dried with a Kimwipe to remove all fungicides and/or other contaminants, and then returned to the plate. The top filter paper layer is placed on the seeds to retain moisture after cleaning. Using a cutting utensil, e.g., a razor, the seeds are then individually removed from the plates and the seed coat removed and discarded. The dark seed tip cap is also removed with the remainder of the seed coat during this process. The endosperm and embryo are separated and immediately immersed into separate aliquots of liquid nitrogen and then separate coin envelopes. After the desired number of seeds are harvested from each plate, the coin envelopes are transferred directly to a −80° C. freezer for storage.

The number of seeds harvested in the 12-hour subgroup may vary. For each subgroup replicate, 10 seeds can be harvested twice, such that a total of 4 tissue samples are collected for each subgroup replicate, e.g., a first embryonic tissue sample, a second embryonic tissue sample, a first endosperm tissue sample, and a second endosperm tissue sample. FIG. 1 shows a diagram of this tissue harvesting scheme 100. As shown, 20 seeds can be harvested from each replicate plate 102, 104 within each subgroup. The embryos and endosperms can be harvested from each seed and placed into separate conical tubes 106, 108, 110, 112, 114, 116, 118, 120 filled at least partially with liquid nitrogen. From the first replicate plate 102, the embryos from 10 seeds may be harvested and placed into conical tube 106. From the same set of 10 seeds, the endosperms may be harvested and placed into conical tube 108. Also from the first replicate plate 102, the embryos from a second set of 10 seeds may be harvested and placed into conical tube 110. From the same second set of 10 seeds, the endosperms may be harvested and placed into conical tube 112. This process can be repeated for the second replicate plate 104, with the tissue samples placed into conical tubes 114-120. After freezing, the tissue samples from conical tubes 106, 108, 110, 112, 114, 116, 118, 120 may be placed into coin envelopes 122, 124, 126, 128, 130, 132, 134, 136, respectively. Coin envelopes are not specifically required, as other containers, e.g., microcentrifuge tubes, can be used to hold the tissue samples after harvested and freezing.

After about 24 hours of incubation, tissue may be harvested from the embryo and/or endosperm of the seeds assigned to the 24-hour subgroup within each treatment and control group. The harvesting methods employed and number of seeds harvested from each 24-hour subgroup are the same relative to the 12-hour subgroup.

After about 72 hours, the subgroups remaining in the incubator may be exposed to light by removing the top layer of filter paper. Instead of discarding the top filter paper, it may be inserted below the seedlings, such that two layers of filter paper remain in each plate. From this point on, the seedlings can be exposed to night/day cycles defined by alternating 12-hour periods of light and dark. Throughout the incubation period, the plates may be rotated within the incubator to ensure that the seedlings are exposed to the light source(s) evenly. The manner in which the seedlings can be rotated may vary depending on the specific incubator used and its settings. For example, seedlings may be rotated more frequently in some incubators than others. Incorrect rotation of the seedlings may cause insufficient growth, and inconsistent rotation between the seedlings may lead to inaccurate results.

After about 96 hours, tissue may be harvested from the radicle of the developing seedlings assigned to the 96-hour subgroup within each treatment and control group. The radicle is the first portion of the seedling to emerge from the seed during germination. As before, the harvested tissue samples may be placed into respective liquid nitrogen aliquots and coin envelopes.

After about 120 hours, tissue may be harvested from the radicle and the coleoptile of the developing seedlings assigned to the 120-hour subgroup within each treatment and control group. The coleoptile is a sheath that forms around the tip of the emerging stem. The coleoptile is only harvested if the coleoptile would separate from the seedling by cutting the base of the coleoptile. The harvested tissue samples are placed into respective coin envelopes and liquid nitrogen aliquots consistent with the previously described harvesting procedures.

After about 144 hours, tissue may be harvested from the radicle and the coleoptile of the developing seedlings assigned to the 144-hour subgroup within each treatment and control group. Consistent with the harvesting procedure applied at the 120-hour timepoint, the coleoptiles are only harvested if they can be separated from the seedling by cutting the base of the coleoptiles. The radicles can be harvested after the coleoptiles.

Figure 2:
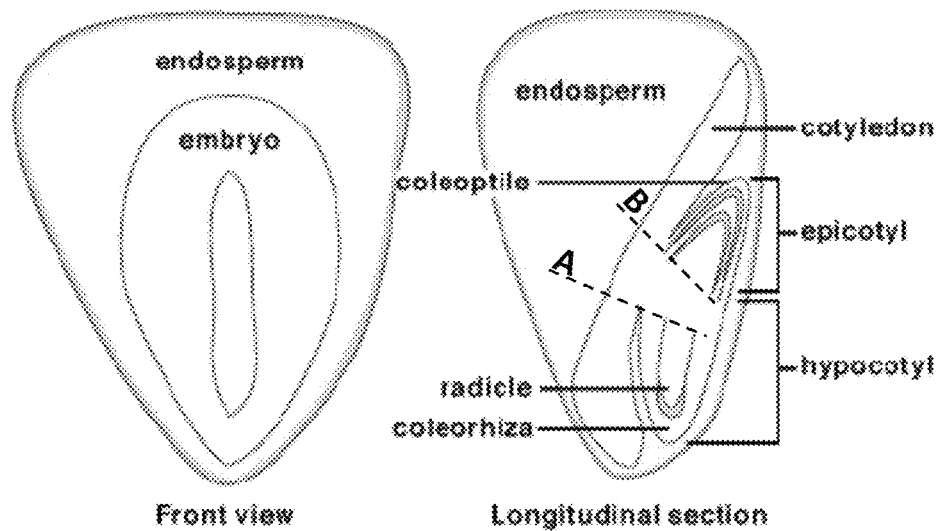
FIG. 2 is an illustration of the seedling tissues harvested for RNA extraction at multiple timepoints in accordance with an example embodiment of the present invention.

Harvesting tissue from the specific plant parts described herein at the particular timepoints disclosed above may be critical to obtaining RNA samples containing transcriptional data regarding developmental processes not visible to the naked eye. For instance, RNA isolated from tissue harvested from the radicle at 96 hours and the coleoptile at 144 hours may contain transcriptional data that reveals one or more subsets of genes particularly responsible for the development of such plant parts and/or the plant parts' sensitivity to one or more PGRs or PGR components. Harvesting other plant parts at the specified timepoints may produce less meaningful transcriptional data with respect to the specific genes that are either upregulated or downregulated in response to certain PGRs or components thereof. Accordingly, precisely harvesting the correct plant parts at the timepoints provided herein may be imperative. FIG. 2. is an illustration of the seedling tissues harvested for RNA extraction at various timepoints, showing a front view and a longitudinal section view of a seedling. As shown, the endosperm may encompass the embryo. The coleoptile and radicle may extend in opposite directions within the epicotyl and hypocotyl, respectively. The radicle can be removed at the 96, 120 and/or 144 hour timepoints by cutting along the base of the radicle at line A, and the coleoptile can be removed at the 120 and/or 144 hour timepoints by cutting along the base of the coleoptile at line B. Incorrect cut placement can result in excess tissue removed from the seedling, which may contaminate the results. To some extent, the excised tissue may inevitably vary from seedling to seedling despite consistent and precise cutting, as germination rates may not be identical even under identical growth conditions. Supplemental measures may thus be implemented to improve the consistency of tissue removal. For instance, randomized seed selection among seedling replicates may be implemented during processing to address inherent variation in the rate of germination.

Total RNA can then be extracted from each of the frozen tissue samples to analyze transcriptional effects of each PGR at each timepoint. The techniques employed to extract RNA may vary and may generally encompass standard techniques employed in academic and commercial settings. In various embodiments, RNA extraction may involve plant tissue homogenization, cell growth, phase separation, RNA precipitation, RNA washing and re-dissolving, followed by spectrophotometric analysis. In some examples, total RNA can be extracted from each tissue sample via a TRIzol® extraction protocol. According to an example of such a protocol, each tissue sample can be placed in a microcentrifuge tube and mixed with about 1 mL of TRIzol® until the mixture is homogenous. Chloroform may then be admixed with the TRIzol® mixture and again mixed until homogenous. Mixing can be performed by pipetting and/or vortexing. Each tissue sample can then be centrifuged and the resulting aqueous phase retained. RNA can be precipitated from the retained aqueous phase using isopropanol, followed by incubation on ice and another round of centrifugation. The supernatant is removed, leaving only a pellet of RNA, which can be washed with ethanol and centrifuged again. After removal of the supernatant, the pellets can be air dried and then dissolved with RNase-free water. To remove any DNA contaminants, each RNA sample can be treated with a DNase, such as Ambion TURBO™DNase, sold by ThermoFisher Scientific, according to the standard protocols provided with the DNase product. The concentration of each RNA sample can be determined by UV spectroscopy.

The RNA samples isolated according to the methods provided herein can be used for fingerprinting transcriptional signatures at each timepoint for each treatment group. Particular implementations may employ RNA sequencing, e.g., Illumina® whole genome sequencing, to determine changes in the expression level of one or many genes, which may be grouped according to molecular function and/or association with specific plant growth processes. In this manner, the transcriptional effect of each PGR at each timepoint may be determined. Such analysis may identify the specific developmental stages most impacted by certain PGRs or components thereof. In response to the data obtained, PGR formulations may be adjusted, for example by increasing the proportion of one or more PGR components. In addition or alternatively, the time at which each PGR is applied to the germinating seeds/seedlings may also be adjusted. For example, RNA sequencing data collected at the 120- and 144-hour timepoints shows that PGR treatment can be associated with increased expression of genes in coleoptile tissue that are involved in common metabolic processes and plant functions, DNA replication, protein synthesis, and cytokinin regulation. Accordingly, supplying nascent seedlings with a PGR at the 120- and 144-hour timepoints may be important to promoting such cellular processes. RNA sequencing data collected from the radicle at the 144-hour timepoint also shows that IBA treatment is associated with increased expression of a gene that codes for a phosphopantothenate-cysteine ligase protein, which catalyzes the biosynthesis of coenzyme A, which is important for respiration. Thus, a PGR formulation high in IBA content may be produced and applied to seedlings at or near the 144-hour timepoint to enhance the upregulation of the phosphopantothenate-cysteine ligase protein to promote healthy respiration.

Figure 3:
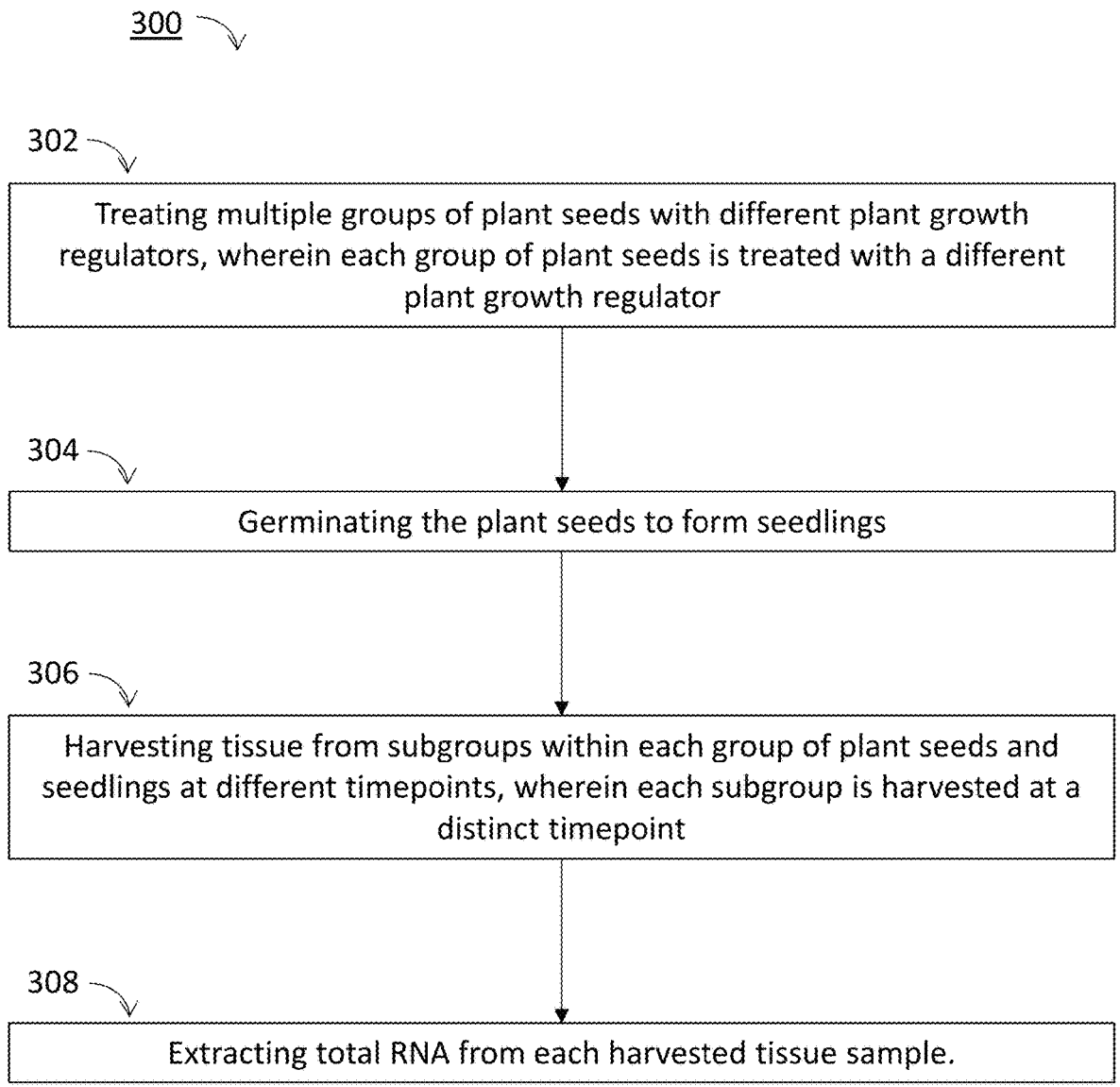
FIG. 3 is a flow diagram of a method performed in accordance with principles of the present disclosure.

FIG. 3 is a flow diagram of a method 300 performed in accordance with principles of the present disclosure. The example method 300 shows the steps that may be utilized for collecting plant tissue and isolated RNA therefrom to obtain gene expression data revealing the effectiveness of one or more PGRs during germination.

In the embodiment shown, the method 300 begins at block 302 by "treating multiple groups of plant seeds with different plant growth regulators, wherein each group of plant seeds is treated with a different plant growth regulator." Plant growth regulators (PGRs) can comprise proprietary mixtures, proprietary products, or components of PGRs, e.g., kinetin or GA. The number and type of seeds treated with the PGRs may vary. In at least one example, treatment groups may comprise 30 maize seeds.

At block 304, the method involves "germinating the plant seeds to form seedlings." Germination may be accomplished by incubating the seeds at about 15.5° C. Seeds may be initially incubated in total darkness, but later transitioned to alternating periods of exposure to light and dark.

At block 306, the method involves "harvesting tissue from subgroups within each group of plant seeds and seedlings at different timepoints, wherein each subgroup is harvested at a distinct timepoint." The specific plant parts harvested may vary from timepoint to timepoint. In some examples, the seeds and seedlings are harvested at five timepoints, beginning at about 12 hours and ending at about 144 hours. In some examples, additional timepoints may be added between 12 and 144 hours and/or the timepoints may be extended beyond 144 hours. In some embodiments, one or more additional timepoints may be added prior to 12 hours, e.g., between 2, 4, 6, 8 10 and 12 hours.

At block 308, the method involves "extracting total RNA from each harvested tissue sample." RNA extraction may be performed using TRIzol® reagent and chloroform. In some embodiments, a commercial RNA extraction kit, e.g., RNeasy Mini Kit, sold by Qiagen, may be used to extract RNA from each tissue sample.

Figure 4:
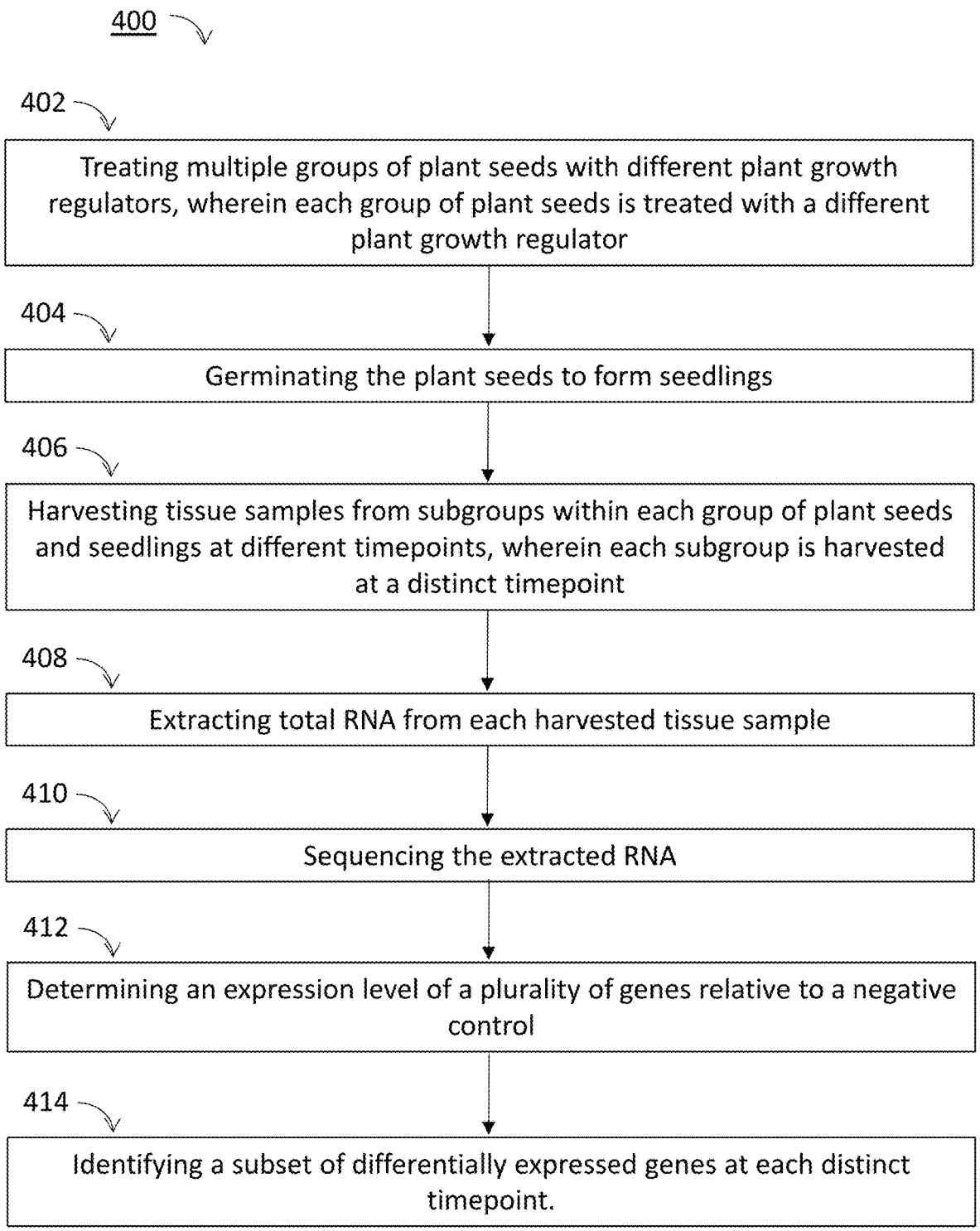
FIG. 4 is a flow diagram of another method performed in accordance with principles of the present disclosure.

FIG. 4 is a flow diagram of a method 400 performed in accordance with principles of the present disclosure. The example method 400 shows the steps that may be utilized for collecting plant tissue, isolated RNA therefrom, and obtain gene expression data indicative of the effectiveness of one or more PGRs during germination.

In the embodiment shown, the method 400 begins at block 402 by "treating multiple groups of plant seeds with different plant growth regulators, wherein each group of plant seeds is treated with a different plant growth regulator."

At block 404, the method involves "germinating the plant seeds to form seedlings."

At block 406, the method involves "harvesting tissue samples from subgroups within each group of plant seeds and seedlings at different timepoints, wherein each subgroup is harvested at a distinct timepoint."

At block 408, the method involves "extracting total RNA from each harvested tissue sample."

At block 410, the method involves "sequencing the extracted RNA."

At block 412 the method involves "determining an expression level of a plurality of genes relative to a negative control."

At block 414, the method involves "identifying a subset of differentially expressed genes at each distinct timepoint."

EXAMPLES

Maize Trial 1

This study applied 5 different PGRs to separate treatment groups each comprised of 30 maize seeds. A negative control group of 30 maize seeds was exposed to a control solution devoid of any PGRs. The ability to germinate the seeds and harvest the desired tissues from the seeds and nascent seedlings at 5 timepoints was evaluated, and the total RNA extracted, sequenced and analyzed. This study revealed that maize seeds treated with various PGRs can be germinated, and the desired tissues may be harvested from most germinated seeds/seedlings between 12 and 144 hours after initiation of the incubation period. RNA-based gene expression analysis revealed several molecular processes that were differentially impacted by PGR application.

Ten plates were prepared for each of the 6 groups evaluated (5 treatment groups+1 control group). Each test group included 5 subgroups, each subgroup corresponding to 1 of the 5 harvesting timepoints. Replicates of each subgroup were prepared, such that each of the 5 subgroups of seeds occupied two plates. Group 1 served as the untreated negative control group. Group 2 was treated with a first PGR composition ("PGR 1") that includes active components containing 0.09 wt % cytokinin (kinetin), 0.03 wt % GA, and 0.045 wt % IBA. Group 3 was treated with kinetin. Group 4 was treated with GA. Group 5 was treated with IBA. Group 6 was treated with a second PGR composition ("PGR 2") that includes active components containing 0.11 wt % CPPA and 0.01 wt % cytokinin (kinetin).

Stock solutions of the treatments were prepared, each including equal amounts of propylene glycol, which was used to dissolve the kinetin. The amount of each treatment substance applied per seed varied between, but not within, the treatment groups. As shown below in Table 1, the control group was untreated. Each seed within group 2 was treated with 1.2 μL of the PGR 1. Each seed within group 3 was treated with 1.14 μg of kinetin. Each seed within group 4 was treated with 0.572 μg of GA. Each seed within group 5 was treated with 0.381 μg of IBA. Each seed within group 6 was treated with 1.7 μL of PGR 2.

TABLE 1

| Plate # | Treatment # | Treatment | Total Amount (uL or ug) applied per seed | Time Point (after application) | Tissue sampled | Daylight |
|---|---|---|---|---|---|---|
| 1 | 1 | Neg. Control | — | 12 h | Embryo | Dark |
| 2 | 1 | Neg. Control | — | 24 h | Embryo | Dark |
| 3 | 1 | Neg. Control | — | 96 h | Radicle | 12 h light/ 12 h dark |
| 4 | 1 | Neg. Control | — | 120 h | Radicle, Coleoptile | 12 h light/ 12 h dark |
| 5 | 1 | Neg. Control | — | 144 h | Radicle, Coleoptile | 12 h light/ 12 h dark |
| 6 | 2 | PGR 1 | 1.2 | 12 h | Embryo, Endosperm | Dark |
| 7 | 2 | PGR 1 | 1.2 | 24 h | Embryo, Endosperm | Dark |
| 8 | 2 | PGR 1 | 1.2 | 96 h | Radicle | 12 h light/ 12 h dark |
| 9 | 2 | PGR 1 | 2.2 | 120 h | Radicle, Coleoptile | 12 h light/ 12 h dark |
| 10 | 2 | PGR 1 | 1.2 | 144 h | Radicle, Coleoptile | 12 h light/ 12 h dark |

TABLE 1-continued

| Plate # | Treatment # | Treatment | Total Amount (uL or ug) applied per seed | Time Point (after application) | Tissue sampled | Daylight |
|---|---|---|---|---|---|---|
| 11 | 3 | Kinetin | 1.14 | 12 h | Embryo, Endosperm | Dark |
| 12 | 3 | Kinetin | 1.14 | 24 h | Embryo, Endosperm | Dark |
| 13 | 3 | Kinetin | 1.14 | 96 h | Radicle | 12 h light/ 12 h dark |
| 14 | 3 | Kinetin | 1.14 | 120 h | Radicle, Coleoptile | 12 h light/ 12 h dark |
| 15 | 3 | Kinetin | 1.14 | 144 h | Radicle, Coleoptile | 12 h light/ 12 h dark |
| 16 | 4 | GA | 0.572 | 12 h | Embryo, Endosperm | Dark |
| 17 | 4 | GA | 0.572 | 24 h | Embryo, Endosperm | Dark |
| 18 | 4 | GA | 0.572 | 96 h | Radicle | 12 h light/ 12 h dark |
| 19 | 4 | GA | 0.572 | 120 h | Radicle, Coleoptile | 12 h light/ 12 h dark |
| 20 | 4 | GA | 0.572 | 144 h | Radicle, Coleoptile | 12 h light/ 12 h dark |
| 21 | 5 | IBA | 0.381 | 12 h | Embryo, Endosperm | Dark |
| 22 | 5 | IBA | 0.381 | 24 h | Embryo, Endosperm | Dark |
| 23 | 5 | IBA | 0.381 | 96 h | Radicle | 12 h light/ 12 h dark |
| 24 | 5 | IBA | 0.381 | 120 h | Radicle, Coleoptile | 12 h light/ 12 h dark |
| 25 | 5 | IBA | 0.381 | 144 h | Radicle, Coleoptile | 12 h light/ 12 h dark |
| 26 | 6 | PGR 2 | 1.7 | 12 h | Embryo, Endosperm | Dark |
| 27 | 6 | PGR 2 | 1.7 | 24 h | Embryo, Endosperm | Dark |
| 28 | 6 | PGR 2 | 1.7 | 96 h | Radicle | 12 h light/ 12 h dark |
| 29 | 6 | PGR 2 | 1.7 | 120 h | Radicle, Coleoptile | 12 h light/ 12 h dark |
| 30 | 6 | PGR 2 | 1.7 | 144 h | Radicle, Coleoptile | 12 h light/ 12 h dark |

The seeds in each group were incubated at 15.5° C. and harvested at 5 timepoints. The first subgroup within each group was harvested after 12 hours of incubation, the second subgroup after 24 hours, the third subgroup after 96 hours, the fourth subgroup after 120 hours, and the fifth subgroup after 144 hours. The embryo and/or endosperm was harvested in each of the first and second subgroups, the radicle harvested from each of the third subgroups, and the radicle and/or coleoptile harvested from each of the fourth and fifth subgroups. All seeds were incubated in the dark for the first 72 hours, after which alternating 12-hour periods of light and dark were initiated and maintained through the 144-hour timepoint.

At the 12-hour timepoint and 24-hour timepoint, the embryo and/or endosperm from the seeds in subgroups 1 and 2 were harvested. At the 96-hour timepoint, the radicle was harvested from most seeds in subgroup 3, except for 6 seeds that showed minimal or non-existent radicle emergence. The seeds that did not grow radicles after 96 hours did not correspond to any particular treatment type, as 1 seed from each group did not show radicle emergence. At the 120-hour timepoint, the radicle and coleoptile was harvested from most seeds in subgroup 4, except for a small number that did not germinate. Group 2 included 2 seeds that were not harvestable, group 3 included 2 non-harvestable seeds, group 4 included 1 non-harvestable seed, and group 6 included 1 non-harvestable seed. At the 144-hour timepoint, the radicle and coleoptile were harvested from most seeds in subgroup 5, except for 1 seed in group 5 that did not germinate and 2 seeds in group 6 that did not germinate.

The harvested tissue samples were immediately frozen in liquid nitrogen and transferred to a −80° C. freezer. Total RNA was then extracted using the TRIzol® extraction protocol described herein. RNA sequencing libraries were prepared for each of the samples, which were used to perform whole-genome RNA sequencing. Expression data for 39,460 different genes was obtained and analyzed to identify which genes were differentially expressed relative to control samples at the timepoints and tissue types sampled and in response to the different treatments applied to each test group. Upregulated genes were defined as genes expressed at a ratio of 2:1 relative to the control, and downregulated genes were defined as genes expressed at a ratio of 0.5:1 relative to the control, based on the quantity of mRNA transcripts produced. Using these standards, the most upregulated and downregulated genes were identified, along with the basic functions of the proteins encoded by such genes, thereby revealing cellular processes most likely affected by the tested PGRs and PGR components in specific tissues at particular timepoints during seed germination and seedling development. The number of upregulated/downregulated genes at each timepoint for each tissue type in response to the various PGRs was also determined to obtain a snapshot of the transcriptional effect of each PGR and PGR component.

Filtering the expression data to identify the most expressed genes at each timepoint for each tissue type in each treatment group revealed differentially expressed genes that code for various proteins. For example, at the 96-hour timepoint, radicle tissue in Group 2 showed significant upregulation of genes coding for a non-specific lipid-transfer protein, an F-box domain-containing protein, a lipid binding protein, a class III peroxidase 68 protein, an N-acetyltransferase and a transcription factor protein, a protease inhibitor/seed storage/LTP family protein, peroxidase 52, a cytochrome P450 family protein, an anther-specific proline-rich protein APG, and a helix-loop-helix DNA-binding domain-containing protein. Several of the aforementioned proteins play a role in plant growth and development. For instance, the non-specific lipid-transfer protein (expressed at a ratio of 73.3:1 relative to the control), plays a role in resistance to biotic and abiotic stress, sexual reproduction, seed development, and germination. Proteins in the F-box family and the class III peroxidase play a role in plant growth and development in response to abiotic and biotic stresses. Peroxidase 52 plays a role in $H_2O_2$ removal and the environmental stress response, as well as nutrient uptake. Proteins in the cytochrome 450 family catalyze reactions in growing tissue, primarily in the pith or cortex of cell division in the root, and catalyze reactions important to plant growth by stimulating the production of hormones and amino acid precursors. The anther-specific proline-rich protein APG promotes lipid biosynthesis, specifically for cell membrane production. The most expressed gene codes for Arabinogalactan, a protein generally known for stimulating embryo development and promoting root growth, and β-glucosidase, a protein that catalyzes glucose release.

At the 120-hour timepoint, radicle tissue treated in Group 2 showed significant upregulation of genes coding for an ATP-binding cassette sub-family G member 2 protein, a TCP family transcription factor-containing protein, a cyclopropane fatty acid synthase, a sulfate transporter 1.2, inositol polyphosphate-5-phosphatase, homeobox-leucine zipper ROC2 protein, a regulator of chromosome condensation protein, a nucleotide binding protein, a glycosyltransferase protein, and an MDR-like ABC transporter protein. The ATP-binding cassette sub-family G member 2 protein promotes intracellular transport. The TCP family transcription factor-containing protein is involved in cell proliferation and cellular signaling. The cyclopropane fatty acid synthase is responsible for the production of CFAs, which play a physiological role in temporal energy storages as well as membrane fluidity during cell growth phases. The sulfate transporter 1.2 protein mediates the uptake of environmental sulfur by plant roots. Inositol polyphosphate-5-phosphatase generates signaling molecules crucial for plant growth and development, including phospholipids conducive to promotion of root growth, vascular development, and response to environmental stimuli. The homeobox-leucine zipper ROC2 protein is a transcription factor involved in abiotic stress responses such as water and light stress. The ROC2 protein is also involved in the de-etiolation process. The regulator of chromosome condensation protein binds with chromatin in specific regions and allows for increased gene expression. The MDR-like ABC transporter protein is linked with the transport of auxins, which are often expressed during early root development, especially in the lateral and root hair regions.

At the 120-hour timepoint, coleoptile tissue treated in Group 2 showed significant upregulation of genes coding for pyruvate decarboxylase isozyme 1, N-acetyltransferase and transcription factor, NADP-dependent oxidoreductase P1, and cis-zeatin O-glucosyltransferase. During plant growth and development, pyruvate decarboxylase isozyme 1 converts pyruvate to acetaldehyde and carbon dioxide, N-acetyltransferase and transcription factor transfers acetyl groups from acetyl-CoA to arylamines, NADP-dependent oxidoreductase P1 promotes zinc ion binding and oxidoreductase activity, and cis-zeatin O-glucosyltransferase exhibits transferase activity, catalyzes the formation of product from cis-zeatin, and regulates active-versus-storage forms of cytokinin.

At the 120-hour timepoint, coleoptile tissue treated in Group 2 also showed significant downregulation (less than 0.1:1 expression ratio relative to the control) of genes coding for the OSE3 protein, a P-type R2R3 Myb protein, a membrane protein, another F-box domain-containing protein, and heat stress transcription factor A-2a. The OSE3 protein is a leucine zipper protein that regulates transcriptional activity during germination. The P-type R2R3 Myb protein is a DNA-binding protein that may be implicated in cellular morphogenesis and signaling transduction. The F-box domain-containing protein is involved in ubiquitination/degradation, regulation of hormonal responses and seedling development. The heat stress transcription factor A-2a protein is involved in transcriptional regulation and binds heat shock promoter elements, which help plants respond to rising temperatures.

At the 144-hour timepoint, radicle tissue treated in Group 2 showed significant upregulation of genes coding for a protein of unknown function (60.8:1 relative to the control), an anther-specific proline-rich APG protein, a class III peroxidase 106 protein, a GDSL-motif lipase/hydrolase, inosine-5'-monophosphate dehydrogenase, phosphopantothenate-cysteine ligase, a class III peroxidase 30 protein, cysteine protease ATG4B, a transcription factor, and cytochrome P450 CYP86A34. The class III peroxidase 106 protein may play a role in physiologics. The GDSL-motif lipase/hydrolase is involved in regulation of plant development, morphogenesis and hormonal pathways. Inosine-5'-monophosphate dehydrogenase play a role in cellular proliferation, especially related to nucleic acid synthesis, signal transduction, energy transfer, and glycoprotein synthesis. Phosphopantothenate-cysteine ligase catalyzes the biosynthesis of coenzyme A, which is important for respiration. The class III peroxidase 30 protein is involved in a diverse range of functions in many physiological processes that occur throughout the plant life cycle. Cytochrome P450 CYP86A34 catalyzes reactions in the pith or cortex of cell division occurring in the plant root.

At the 144-hour timepoint, coleoptile tissue treated in Group 2 showed significant upregulation (greater than 10:1 expression ratio relative to the control) of genes coding for a UPF0497 membrane protein, cytokinin-N-glucosyltransferase 1, β-expansin 1a, and an F-box domain-containing protein. The UPF0497 membrane protein promotes DNA binding and RNA polymerase II transcription factor activity, cytokinin-N-glucosyltransferase 1 promotes N-glucosylation of cytokinins that play a role in hormone homeostasis, β-expansin 1a plays a role in cell wall organization, loosening and enlargement, and the F-box domain-containing protein is involved in protein ubiquitination/degradation, regulation of hormonal responses and seedling development.

At the 144-hour timepoint, coleoptile tissue treated in Group 2 also showed significant downregulation (less than 0.1:1 expression ratio relative to the control) of genes coding for a GA C20 oxidase 2 protein, a nucleotidyltransferase protein, a DUF2431 domain-containing protein. The GA C20 oxidase 2 protein catalyzes oxidation in the GA synthesis pathway and the nucleotidyltransferase protein plays a role in translation and transcription during seed germination.

These data indicate, among other things, that in the coleoptile, the PGR composition applied to Group 2 upregulates genes involved in common metabolic processes and plant functions, DNA replication and protein synthesis, regulation of cytokinins. Collectively, the data suggests that the PGR composition may be accelerating germination.

As used herein, the term "about" modifying, for example, the quantity of a component in a composition, concentration, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

Similarly, it should be appreciated that in the foregoing description of example embodiments, various features are sometimes grouped together in a single embodiment for the purpose of streamlining the disclosure and aiding in the understanding of one or more of the various aspects. These methods of disclosure, however, are not to be interpreted as reflecting an intention that the claims require more features than are expressly recited in each claim. Rather, as the following claims reflect, inventive aspects lie in less than all features of a single foregoing disclosed embodiment, and each embodiment described herein may contain more than one inventive feature.

Although the present disclosure provides references to preferred embodiments, persons skilled in the art will recognize that changes may be made in form and detail without departing from the spirit and scope of the invention.

What is claimed is:

1. A method of treating plant tissue, the method comprising:
    treating plant seeds with a plant growth regulator composition;
    harvesting tissue samples from seedlings derived from the plant seeds after the plant seeds have germinated; and
    extracting RNA from each harvested tissue sample,
        wherein the plant growth regulator composition comprises about 0.03 wt % to about 0.2 wt % kinetin, about 0.005 wt % to about 0.15 wt % gibberellic acid, and about 0.008 wt % to about 0.17 wt % indole-3-butyric acid.

2. The method of claim 1, wherein harvesting tissue samples comprises harvesting at least a portion of an embryo, an endosperm, a radicle, a coleoptile, or a combination thereof.

3. The method of claim 1, wherein extracting RNA comprises extracting total RNA.

4. The method of claim 3, further comprising performing whole-genome sequencing of the total RNA.

5. The method of claim 1, wherein harvesting tissue samples comprises harvesting the tissue samples at multiple timepoints.

6. The method of claim 5, wherein the timepoints comprise about 12 hours after planting, about 24 hours after planting, about 96 hours after planting, about 120 hours after planting, and/or about 144 hours after planting.

7. The method of claim 5, wherein the multiple timepoints are each separated by at least 12 hours.

8. The method of claim 5, wherein a unique tissue sample is harvested at each of the timepoints.

9. The method of claim 5, wherein each of the multiple timepoints corresponds to a different developmental stage of the seedlings.

10. The method of claim 1, wherein the plant seeds comprise one or more of corn seeds, bean seeds, wheat seeds, barley seeds, or alfalfa seeds.

11. The method of claim 1, wherein treating plant seeds with a plant growth regulator composition comprises applying the plant growth regulator composition to the seeds and incubating the seeds for a period thereafter.

12. The method of claim 11, wherein the period is at least about 12 hours.

13. A method of treating plant tissue, the method comprising:
    treating plant seeds with a first plant growth regulator composition at a first timepoint; and
    treating seedlings derived from the plant seeds with a second growth regulator composition, different than the first plant growth regulator composition, at a second timepoint,
    wherein the first and second plant growth regulator compositions comprise about 0.03 wt % to about 0.2 wt % kinetin, about 0.005 wt % to about 0.15 wt % gibberellic acid, and about 0.008 wt % to about 0.17 wt % indole-3-butyric acid.

14. The method of claim 13, further comprising treating the seedlings with a third plant growth regulator composition, different than the first and second growth regulator compositions, at a third timepoint.

15. The method of claim 13, wherein the first and second timepoints are separated by at least about 12 hours.

16. The method of claim 13, wherein the plant seeds comprise one or more of corn seeds, bean seeds, wheat seeds, barley seeds, and alfalfa seeds.

17. The method of claim 16, wherein the first plant growth regulator composition is different for each of the one or more corn seeds, bean seeds, wheat seeds, barley seeds, and/or alfalfa seeds.

18. The method claim 16, wherein the second plant growth regulator composition is different for each of the one or more corn seeds, bean seeds, wheat seeds, barley seeds, and/or alfalfa seeds.

19. The method of claim 16, further comprising harvesting plant tissue derived from the one or more corn seeds, bean seeds, wheat seeds, barley seeds, and alfalfa seeds at different timepoints.

20. The method of claim 16, wherein the first timepoint is different for each of the one or more corn seeds, bean seeds, wheat seeds, barley seeds, and/or alfalfa seeds.

* * * * *